US010702666B2

United States Patent
Shafer

(10) Patent No.: US 10,702,666 B2
(45) Date of Patent: Jul. 7, 2020

(54) CUSTOMIZABLE FACIAL SEALING SEGMENT FOR RESPIRATORY DEVICE AND METHOD OF CUSTOMIZING

(71) Applicant: KONINKLIJKE PHILIPS N.V., Eindhoven (NL)

(72) Inventor: Sandy Jane Shafer, Pittsburgh, PA (US)

( * ) Notice: Subject to any disclaimer, the term of this patent is extended or adjusted under 35 U.S.C. 154(b) by 1006 days.

(21) Appl. No.: 15/105,608

(22) PCT Filed: Nov. 28, 2014

(86) PCT No.: PCT/IB2014/066419
§ 371 (c)(1),
(2) Date: Jun. 17, 2016

(87) PCT Pub. No.: WO2015/092583
PCT Pub. Date: Jun. 25, 2015

(65) Prior Publication Data
US 2017/0000964 A1    Jan. 5, 2017

Related U.S. Application Data

(60) Provisional application No. 61/918,780, filed on Dec. 20, 2013.

(51) Int. Cl.
*A61M 16/06* (2006.01)
*A61M 16/08* (2006.01)
*A62B 18/02* (2006.01)

(52) U.S. Cl.
CPC ........ *A61M 16/0616* (2014.02); *A61M 16/06* (2013.01); *A61M 16/0633* (2014.02);
(Continued)

(58) Field of Classification Search
CPC .................................... B42F 3/00; B42F 3/03
(Continued)

(56) References Cited

U.S. PATENT DOCUMENTS

| 4,454,881 A | 6/1984 | Huber |
| 4,622,696 A * | 11/1986 | Griffiths ................. A62B 17/04 2/424 |

(Continued)

FOREIGN PATENT DOCUMENTS

| CN | 101056678 A | 10/2007 |
| EP | 1116492 A2 | 7/2001 |

(Continued)

OTHER PUBLICATIONS

Perforated Paper, "More Information about Perforated Paper," (Year: 2006).*

*Primary Examiner* — Rachel T Sippel
*Assistant Examiner* — Benjamin M. Kusiak
(74) *Attorney, Agent, or Firm* — Michael W. Haas

(57) ABSTRACT

A facial sealing segment for a respiratory device includes a sealing flap adapted to sealingly engage the face of a user. The sealing flap is disposed about, and defines, a cutout adapted to receive one or both of the mouth or nares of the user. The facial sealing segment further includes a number of selectively removable portions formed in the sealing flap about the cutout. Each removable portion is defined in the sealing flap by a tear portion. The facial sealing segment may be customized by a method that includes removing at least one of the removable portions by separating the at least one removable portion from the remainder of the sealing flap by severing along the tear portion thereof.

12 Claims, 3 Drawing Sheets

(52) U.S. Cl.
CPC .... *A61M 16/0683* (2013.01); *A61M 16/0816* (2013.01); *A61M 16/0875* (2013.01); *A62B 18/025* (2013.01); *A61M 2016/0661* (2013.01); *A61M 2207/00* (2013.01)

(58) Field of Classification Search
USPC ........... 2/417, 428, 440; 128/206.24, 206.28, 128/207.11, 206.21, 205.25, 204.18, 128/200.24
See application file for complete search history.

(56) References Cited

U.S. PATENT DOCUMENTS

| | | | |
|---|---|---|---|
| 5,673,690 A * | 10/1997 | Tayebi | A41D 13/1115 128/205.27 |
| 5,918,598 A | 7/1999 | Belfer | |
| 6,102,040 A * | 8/2000 | Tayebi | A41D 13/1115 128/205.27 |
| 8,365,734 B1 | 2/2013 | Lehman | |
| 8,869,798 B2 | 10/2014 | Wells et al. | |
| 10,117,599 B2 | 11/2018 | Orr et al. | |
| 2004/0118406 A1 | 6/2004 | Lithgow | |
| 2006/0042629 A1* | 3/2006 | Geist | A61M 16/06 128/206.24 |
| 2006/0101552 A1 | 5/2006 | Lee | |
| 2008/0302365 A1* | 12/2008 | Cohen | A61M 16/06 128/206.12 |
| 2010/0000534 A1* | 1/2010 | Kooij | A61M 16/0666 128/204.18 |
| 2010/0126994 A1* | 5/2010 | Tielbeke | B21D 51/383 220/273 |
| 2011/0005524 A1* | 1/2011 | Veliss | A61M 16/0666 128/206.24 |
| 2011/0132375 A1 | 6/2011 | Thornton | |
| 2011/0197341 A1* | 8/2011 | Formica | A61M 16/0683 2/209.3 |
| 2012/0017911 A1 | 1/2012 | Choi et al. | |
| 2013/0008445 A1 | 1/2013 | Boussignac | |
| 2013/0152938 A1 | 6/2013 | Jablonski | |
| 2013/0199537 A1* | 8/2013 | Formica | A61M 16/0057 128/205.25 |
| 2014/0083427 A1 | 3/2014 | Andrews | |
| 2014/0196720 A1 | 7/2014 | Eury | |
| 2015/0374943 A1* | 12/2015 | Alexani | A61M 16/0616 128/206.24 |

FOREIGN PATENT DOCUMENTS

| | | |
|---|---|---|
| WO | WO9921602 A1 | 5/1999 |
| WO | WO2009143586 A1 | 12/2009 |
| WO | WO2012143828 A1 | 10/2012 |
| WO | WO2013027144 A1 | 2/2013 |
| WO | WO2013055131 A2 | 4/2013 |
| WO | WO2013084110 A1 | 6/2013 |
| WO | WO2013098727 A2 | 7/2013 |
| WO | WO2013108145 A1 | 7/2013 |
| WO | WO2013136221 A1 | 9/2013 |
| WO | WO2014091370 A1 | 6/2014 |

* cited by examiner

CUSTOMIZABLE FACIAL SEALING SEGMENT FOR RESPIRATORY DEVICE AND METHOD OF CUSTOMIZING

CROSS-REFERENCE TO RELATED APPLICATIONS

This patent application claims the priority benefit under 35 U.S.C. § 371 of international patent application no. PCT/IB2014/066419, filed Nov. 28, 2014, which claims the priority benefit under 35 U.S.C. § 119(e) of U.S. Provisional Application No. 61/918,780 filed on Dec. 20, 2013, the contents of which are herein incorporated by reference.

BACKGROUND OF THE INVENTION

1. Field of the Invention

The present invention generally relates to respiratory devices, and more particularly to customizable facial sealing segments for use with such devices. The present invention also relates to methods of customizing a sealing segment of a respiratory device.

2. Description of the Related Art

There are numerous situations where it is necessary or desirable to selectively control the content of matter inhaled by a user. Such situations may arise where environmental conditions necessitate the filtering of particulates from the environment or in instances where a particular flow of gas(es) are to be delivered to a user/patient. For example, it is known to ventilate a patient using a technique known as non-invasive ventilation (NIV). It is also known to deliver continuous positive airway pressure (CPAP) or variable airway pressure, which varies with the patient's respiratory cycle, to treat a medical disorder, such as sleep apnea syndrome, in particular, obstructive sleep apnea (OSA), chronic obstructive pulmonary disease (COPD), or congestive heart failure (CHF).

Non-invasive ventilation and pressure support therapies involve the placement of a patient interface device, which is typically a nasal (covering nose), full face (covering mouth and nose), or oronasal (covering mouth and under the nose), on the face of a patient to interface the ventilator or pressure support system with the airway of the patient so that a flow of breathing gas can be delivered from the pressure/flow generating device to the airway of the patient.

Typically, patient interface devices include a mask shell or some form of support having a cushion attached thereto that contacts and sealingly engages the surface of the patient. The support and cushion are typically held in place by a headgear that wraps around the head of the patient. The support and headgear form the patient interface assembly. A typical headgear includes flexible, adjustable straps that extend from the mask to attach the mask to the patient.

Because such masks are typically worn for an extended period of time, a variety of concerns must be taken into consideration. For example, in providing CPAP to treat OSA, the patient normally wears the patient interface device all night long while he or she sleeps. One concern in such a situation is that the patient interface device is as comfortable as possible, otherwise the patient may avoid wearing the interface device, defeating the purpose of the prescribed pressure support therapy. It is also important that the overall size of the interface device be minimized, so as to not be overly cumbersome on the face of the patient.

Historically, interface devices are produced in several sizes in order to accommodate the wide variety of facial sizes and structures present in the population. As the number of mask sizes provided increases, so does the costs associated with manufacturing, stocking, etc. Accordingly, there is room for improvement in providing interface devices which are able to fit larger segments of the population and/or are able to be readily customized to produce a better fit.

SUMMARY OF THE INVENTION

Accordingly, it is an object of the present invention to provide improved sealing segments as well as respiratory devices utilizing such sealing segments that overcome deficiencies in the known art. Embodiments in accordance with the principles of the present invention provide sealing segments having cutouts with can be readily altered to fit a broader range of user's and/or to better fit a particular user.

As one aspect of the invention, a facial sealing segment for a respiratory device is provided. The sealing segment comprises: a sealing flap adapted to sealingly engage the face of a user, the sealing flap disposed about, and defining a cutout adapted to receive one or both of the mouth or nares of the user; and a number of selectively removable portions formed in the sealing flap about the cutout, each removable portion being defined in the sealing flap by a tear portion.

The sealing flap may comprise a first thickness and the tear portion may comprise a localized thickness less than the first thickness.

The tear portion may comprise a groove formed in the sealing flap.

The groove may be formed in a surface of the sealing flap opposite from a surface which sealingly engages the face of the user.

The tear portion may comprise a plurality of perforations formed in the sealing flap.

The number of removable portions may comprise a first portion adapted to be disposed adjacent a first side of the mouth of the user and a second portion adapted to be disposed adjacent a second side of the mouth of the user.

At least one removable portion of the number of removable portions may comprise a pull tab extending from a surface of the sealing flap opposite from a surface which sealingly engages the face of the user.

At least one removable portion may comprise a sub-removable portion formed therein about the cutout, the sub-removable portion being defined in the at least one removable portion by a sub-tear portion.

The number of removable portions may comprise a single removable portion which completely encompasses, and defines, the cutout.

The cutout may comprise a first cutout adapted to receive the mouth of the user; the sealing flap may further be disposed about, and defines, a second cutout adapted to receive the nares of the user; and the sealing segment may further comprise a number of further removable portions formed in the sealing flap about the second cutout, each further removable portion being defined by a further tear portion.

As another aspect of the invention, a method of customizing a sealing segment of a respiratory device is provided. The method comprises providing a sealing segment comprising: a sealing flap adapted to engage the face of a user, the sealing flap disposed about, and defining a cutout adapted to receive one or both of the mouth or nares of the user; and a number of selectively removable portions formed in the sealing flap about the cutout, each removable portion being defined in the sealing flap by a tear portion. The method further comprises removing at least one removable portion by separating the at least one removable portion from the remainder of the sealing flap by severing along the tear portion.

Removing at least one removable portion by separating the at least one removable portion from the remainder of the sealing flap by severing along the tear portion may comprise removing a first removable portion from a first side of the cutout and removing a second removable portion from a second side of the cutout generally opposite the first side.

Removing at least one removable portion by separating the at least one removable portion from the remainder of the sealing flap by severing along the tear portion may comprise removing a portion of the sealing flap which is adapted to be disposed about the bridge of the nose of the user.

Removing at least one removable portion by separating the at least one removable portion from the remainder of the sealing flap by severing along the tear portion may comprise removing a single removable portion which completely encompasses, and defines, the cutout.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF THE EXEMPLARY EMBODIMENTS

Figure 1:
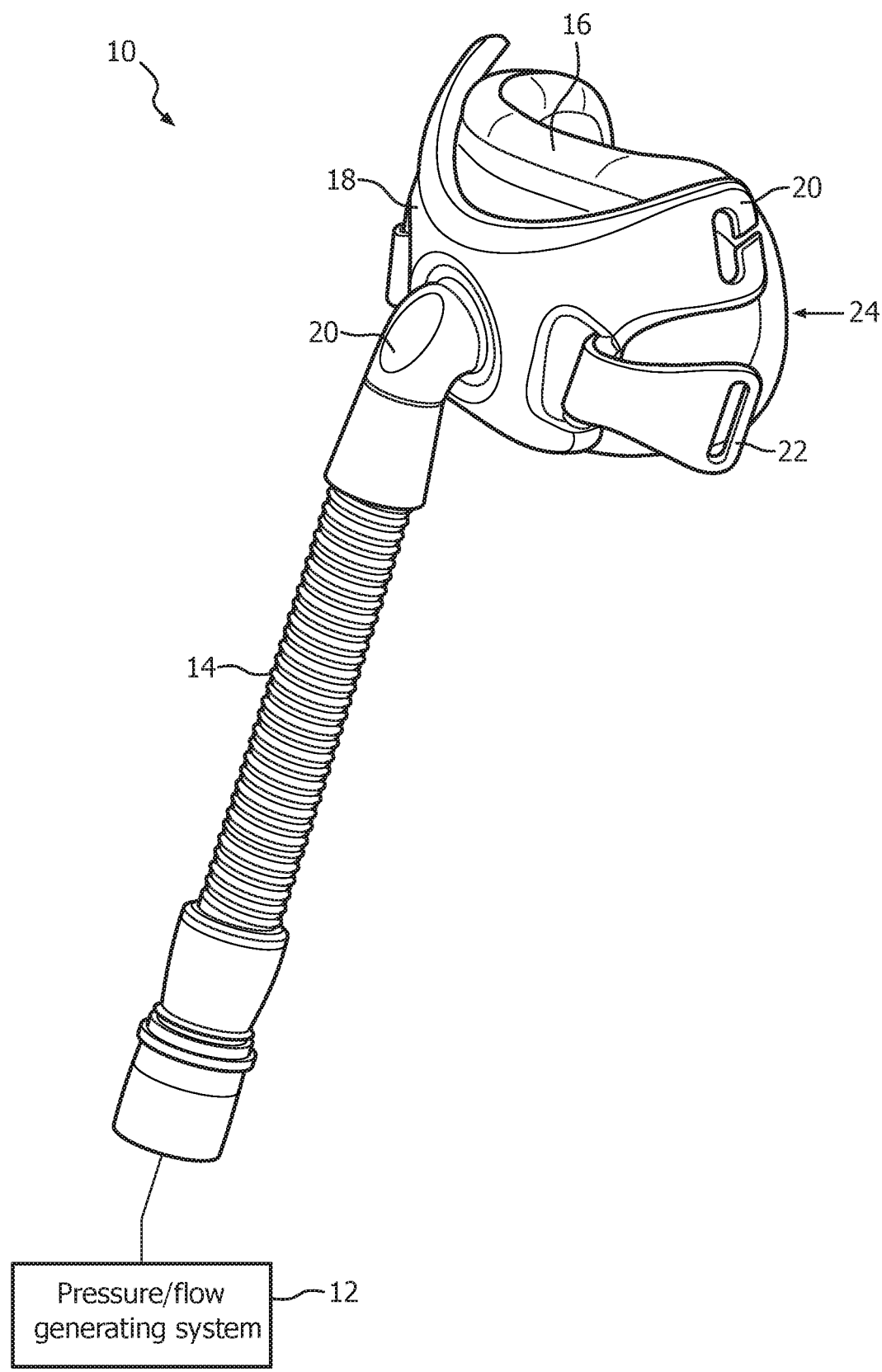
FIG. 1 is a front isometric view of an example embodiment of a patient interface device according to the principles of the present invention shown (schematically) connected to a gas flow/pressure generating system to form a patient interface system.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, "respiratory device" shall be used to refer to any device which sealingly engages about one or both of a user's mouth and/or nose, for selectively controlling the content of matter inhaled by the user. Such devices may include, for example, without limitation, devices for filtering air inhaled by a user (e.g., respirators) and devices used in delivering a flow of gas to the airway of the user (e.g., oxygen masks, CPAP masks, etc.).

As employed herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality) and the singular form of "a", "an", and "the" include plural referents unless the context clearly indicates otherwise.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 2:
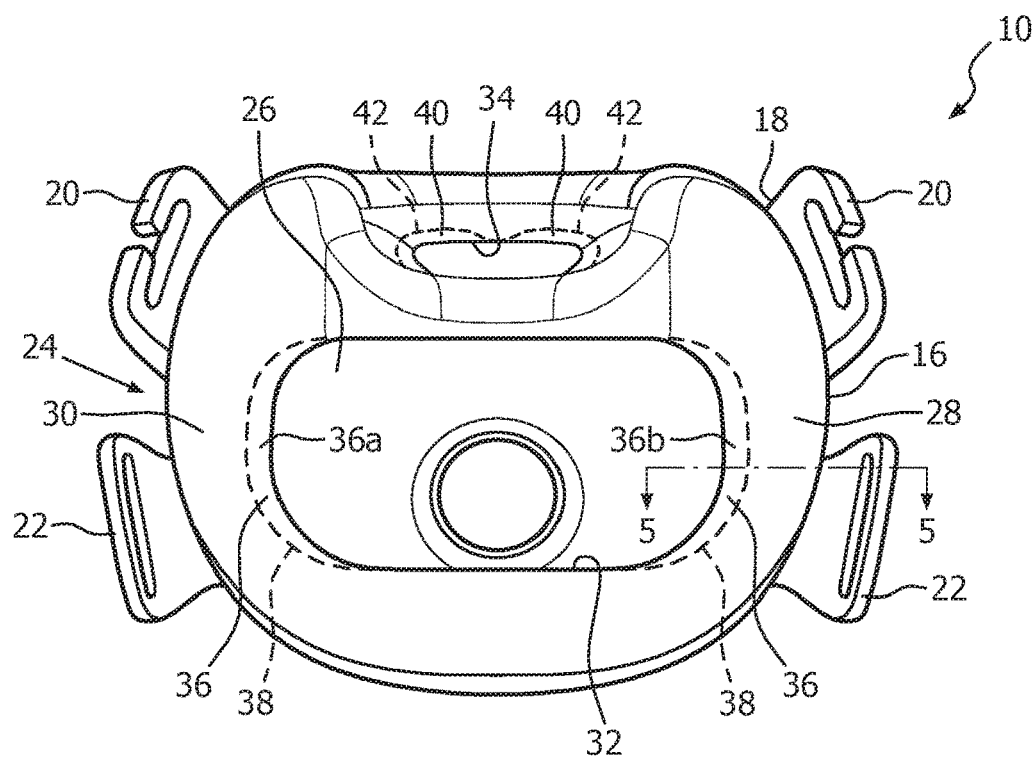
FIG. 2 is an elevation view of the patient facing side of the patient interface device of FIG. 1.

FIGS. 1 and 2 illustrate an exemplary embodiment of a respiratory device in the form of a patient interface device 10 and components thereof according to the principles of the present invention. Patient interface device 10 communicates a flow of breathing gas between the patient's airway and a pressure/flow generating system 12 (shown schematically), such as a ventilator, CPAP device, or variable pressure device, e.g., a BiPAP® device manufactured and distributed by Philips Respironics, Inc. of Pittsburgh, Pa., or an auto-titration pressure support system.

A BiPAP® device is a bi-level device in which the pressure provided to the patient varies with the patient's respiratory cycle, so that a higher pressure is delivered during inspiration than during expiration. An auto-titration pressure support system is a system in which the pressure varies with the condition of the patient, such as whether the patient is snoring or experiencing an apnea or hypopnea. For present purposes, pressure/flow generating system 12 is also referred to as a gas flow generating device, because flow results when a pressure gradient is generated. The present invention contemplates that pressure/flow generating system 12 is any conventional system for delivering a flow of gas to an airway of a patient or for elevating a pressure of gas at an airway of the patient, including the pressure support systems summarized above and non-invasive ventilation systems.

Communicating a flow of breathing gas between the patient's airway and pressure/flow generating system 12 includes delivering a flow of breathing gas to the patient from the pressure/flow generating device and exhausting a flow of gas from the patient to ambient atmosphere. Referring to FIG. 1, the system for delivering a breathing gas to a patient according to the present invention comprises pressure/flow generating system 12 that produces a flow of gas, and a conduit 14, which is also referred to as a patient circuit, having a first end portion (not numbered) operatively coupled to the gas flow generating device and a second end portion (not numbered). Conduit 14 carries the flow of gas from pressure/flow generating device 12 during operation of the system to patient interface device 10, which is coupled to the second end portion of conduit 14. Conduit 14 corresponds to any conduit suitable for communicating the flow of gas form the pressure/flow generating system to the patient interface device. An example of a typical conduit is a flexible tube. A headgear assembly, which is not shown in the figures, attaches patient interface device 10 to the patient's head.

Patient interface device 10 is depicted as an oronasal device which includes a cushion 16 and a shell or frame 18 having a patient side and opposite thereto, an outer side. Attached to frame 18 is a conduit coupling member, such as elbow 20, that couples cushion 16 and frame 18 to conduit 14 so that a flow of gas is communicated to the interior of the patient interface device for subsequent delivery to the patient. Conversely, gas from the patient is communicated from the patient interface device into conduit 14, where an exhaust port (not numbered) may be located. In an exemplary embodiment, frame 18 is formed as a generally rigid member formed from polycarbonate. It is to be understood that the present invention contemplates that one or more of the size, shape, or composition of frame 18 may be varied without varying from the scope of the present invention.

In the illustrated embodiment of FIGS. 1 and 2, frame 18 has a generally x-shape and is provided with upper and lower headgear attaching elements 20, 22, which cooperate with corresponding attachment elements on headgear straps (not illustrated) for securely mounting patient interface device 10 on the head of a user. It is to be understood, however, that the present invention contemplates using any conventional connection assembly to attach a headgear or headgear strap to frame 18 or other suitable arrangement. It is to be further understood that the present invention also contemplates that frame 18 may further include a forehead support portion having headgear attaching elements for connection to further headgear straps. The present invention also contemplates providing a post or other protrusion at the upper portion of the shell, i.e., the portion overlying the bridge of the nose, to which the headgear can be attached.

The present invention contemplates that the headgear suitable for use with patient interface device 10 is any conventional headgear used in the patient interface field. For example, without limitation, a typical headgear assembly comprises a headpiece that overlies a portion of the patient's crania and with headgear straps extending therefrom to adjustably connect the headgear to the mask.

In an exemplary embodiment cushion 16 is formed of a soft, cushiony, elastomeric material, such as silicone, appropriately soft thermoplastic elastomers, closed cell foam, thin materials, or any combination of suitable materials and includes a first portion (not numbered) adapted to be coupled to a mask or frame (such as frame 18 of FIGS. 1 and 2) and receive a flow of gas (such as from pressure/flow generating device 12 of FIG. 1), an opposite second portion 24, and a passage or cavity 26 (FIG. 2) formed therethrough extending between the first portion and second portion 24. Cavity 26 is adapted to conduct the flow of gas generated by pressure/flow generating device 12 (and passed through conduit 14) therethrough to the airway of the user when patient interface device 10 is disposed on the head of the user/patient.

Referring to FIG. 2, second end portion 24 includes a sealing segment 28 which includes a sealing portion or flap 30 which is adapted to sealing engage the face of a user. Sealing flap 30 is disposed about, and defines, a first cutout 32 which is adapted to receive the mouth of the user and a second cutout 34 which is adapted to receive the nares of the user. In other words, when installed on a user/patient, sealing flap 30 generally sealingly engages the face of the user about the mouth and nares of the user. Sealing segment 28 further includes a number of selectively removable portions 36 formed in sealing flap 30 about cutout 32. Each removable portion 36 is defined in sealing flap 30 by a respective tear portion 38 (shown in dashed line) configured to allow for each removable portion to be selectively removed from sealing flap 30 as desired by a user or other person or to remain as a unitary portion of sealing flap 30 if desired. In the example embodiment illustrated in FIG. 2, two of such removable portions 36 are provided, a first portion 36a positioned generally at one end or side of cutout 32 such that it is adapted to be disposed adjacent a first side of the mouth of the user when device 10 is donned by a user, and a second portion 36b positioned generally at the opposite side or end of cutout 32 such that it is adapted to be disposed adjacent a second side of the mouth of the user. It is to be appreciated that such arrangement allows for the width (not labeled) and shape of cutout 32 to be selectively widened if desired to improve the fit of sealing element 28 on the face of a user.

Continuing to refer to FIG. 2, sealing segment 30 may further include a number of further removable portions 40 formed in sealing flap 30 about second cutout 34, with each further removable portion 40 being defined by a further tear portion 42 (shown in dashed line). Such further removable portions allow one or both of the size or shape of second cutout 34 to be customized by a user or other person as desired to better fit device 10 to the user.

Figure 5:
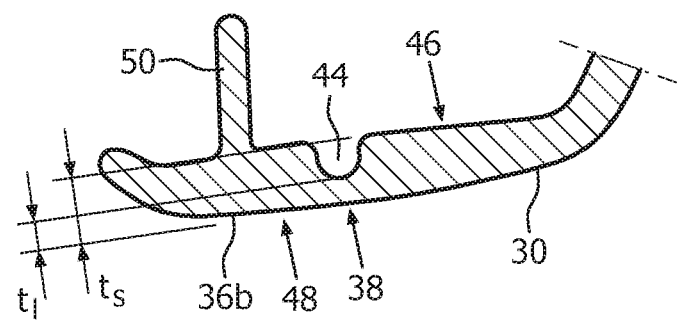
FIG. 5 is a sectional view of the portion of the sealing element of the patient interface device of FIGS. 1 and 2 as taken along the line 5-5 indicated in FIG. 2.

As shown in the sectional view of FIG. 5, tear portion 38 (and similarly tear portion 42) may be formed as a portion within sealing flap 30 having a localized thickness $t_t$ less than an adjacent thickness $t_s$ of sealing flap 30. In the example embodiment illustrated in FIGS. 1, 2 and 5, such difference is provided by forming tear portion 38 as a groove 44 formed in sealing flap 30 on or in an interior surface 46 opposite from an outer surface 48 which sealingly engages the face of the user. It is to be understood that the present invention contemplates that any other suitable arrangement of reduced thickness portion may be employed without varying from the scope of the present invention.

As another mechanism to promote separation of removable portions 36 (or 40) from sealing flap 30, each tear portion 38, 42 may be formed from a plurality of perforations formed in sealing flap 30. Such perforations may be formed completely through sealing flap 30 or may be formed as indentations or other suitable structures formed in one or both of surfaces 46 and 48 of sealing flap 30. Additionally, it is to be understood that the present invention contemplates that any other suitable arrangement which provides for the removable portions 36, 40 to be readily removed from sealing element 30 generally without the need for tools or other instruments may be employed without varying from the scope of the present invention.

Continuing to refer to FIG. 5, in order to assist in removing one of the removable portions, a readily grippable portion, such as pull tab 50 or other suitable structure (e.g., without limitation, a textured surface), may be provided on, or extending from removable portion 36 (or similarly 40).

Figure 3:
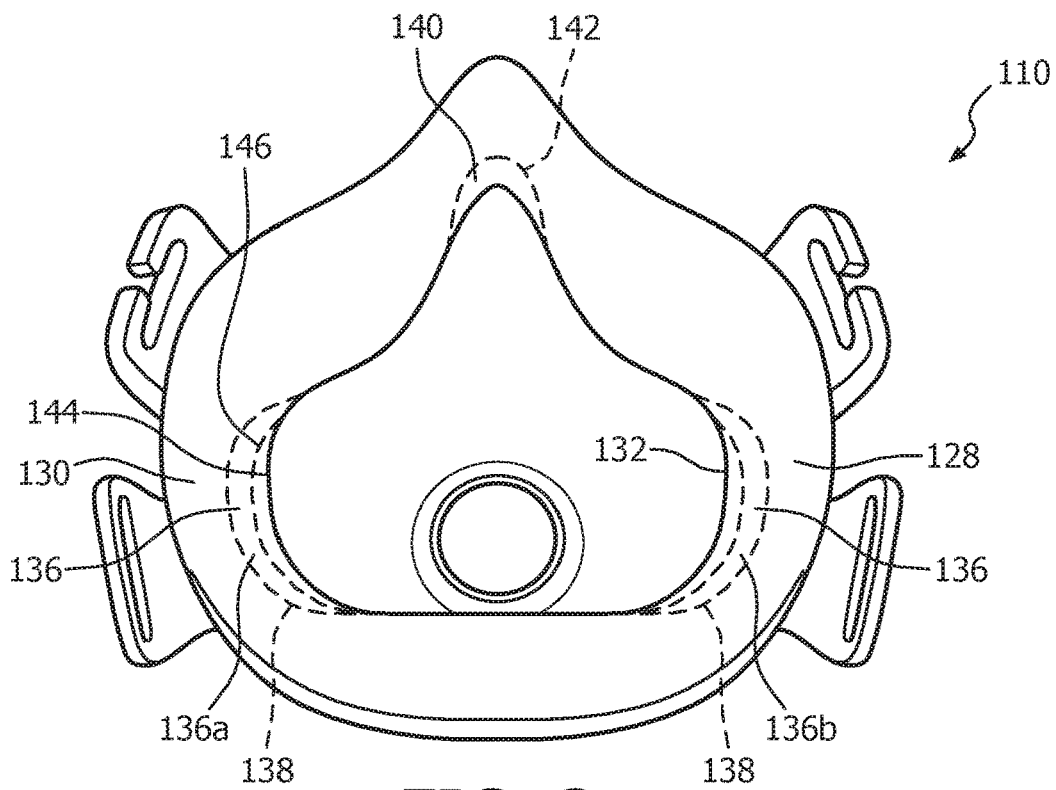
FIG. 3 is an elevation view of the patient side of another example embodiment of a patient interface device according to the principles of the present invention.

FIG. 3 illustrates another example embodiment of a respiratory device 110 according to the principles of the present invention which includes a sealing segment 128 having a sealing flap 130 which surrounds, and defines, a single cutout 132. Sealing segment 128 includes a number of selectively removable portions 136 and 140 defined in sealing flap 130 about cutout 132. Similar to the removable portions 36, 40, previously discussed, each of removable portions 136 and 140 is defined in sealing flap 130 by a respective tear portion 138, 142 (shown in dashed line) configured to allow for each removable portion to be selectively removed from sealing flap 130 as desired by a user or other person. Unlike removable portions 36 and 40 previously discussed, each of removable portions 136a and 136b further comprise a sub-removable portion 144 (only one is labeled in FIG. 3) formed therein about the cutout. Each sub-removable portion is defined in the respective removable portion 136a by a sub-tear portion 146. Each sub-tear portion may be formed in a similar manner as tear portions 38 and 42 previously discussed. It is to be appreciated that such arrangement allows for multiple custom sizes to be selected by a user or other person form a single sealing element.

Figure 4:
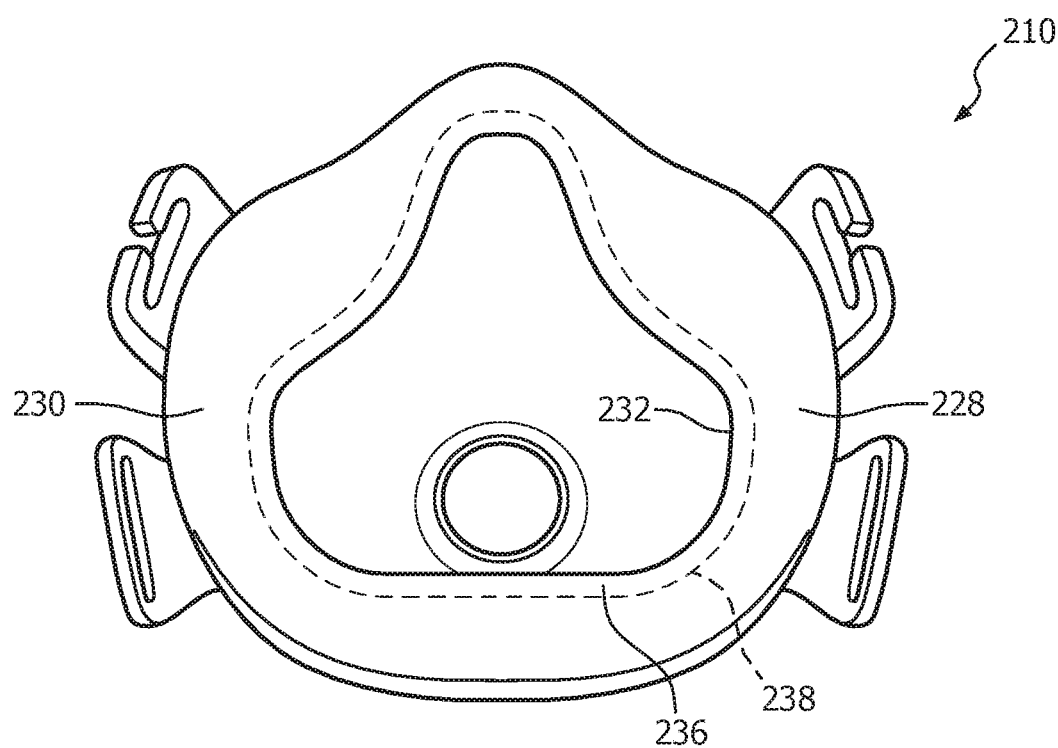
FIG. 4 is an elevation view of the patient side of yet a further example embodiment of a patient interface device according to the principles of the present invention.

FIG. 4 illustrates yet another example embodiment of a respiratory device 210 according to the principles of the present invention which includes a sealing segment 228 having a sealing flap 230 which surrounds, and defines, a single cutout 232. Sealing segment 228 includes a selectively removable portion 236 which completely encompasses, and defines, cutout 232. Removable portion 236 is defined in sealing flap 230 by a tear portion 238 (shown in dashed line) configured to allow for removable portion 236 to be selectively removed from sealing flap 230, thus overall enlarging cutout 232. Although shown as generally providing for the overall enlargement of cutout 232, it is to be appreciated that the present invention contemplates that such arrangement, as well as the arrangements previously discussed, may be used alone or in various combinations to allow for customizing of one or more of the size or shape of a cutout or cutouts provided in a sealing segment.

Although described in conjunction with sealing segments having cutouts of particular shapes and sizes, it is to be understood that the present invention contemplates that the concepts and principles disclosed herein may be readily applied to sealing segments having cutouts of generally any suitable size and/or shape.

Although described primarily in conjunction with respiratory devices used for delivering a flow of gases to a user/patient, it is to be understood that the present invention contemplates that concepts and principles disclosed herein may be readily applied to other respiratory devices (e.g., respirators or other suitable devices) which utilize one or more segments for engaging the face of a user.

It is to be appreciated that the present invention is not intended to be limited to the frame shape described herein but instead may be employed with frames and cushions of various other shapes or designs which utilize a cutout with a rectangular portion as described herein.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A facial sealing segment for a respiratory device, the sealing segment comprising:
    a sealing flap adapted to sealingly engage the face of a user, the sealing flap having an inner edge that is disposed about, and defines a cutout adapted to receive one or both of the mouth or nares of the user; and
    a number of selectively removable portions formed in the sealing flap about the cutout, each removable portion being defined in the sealing flap by a tear portion that extends along a smooth curving line from a first location on the inner edge of the sealing flap to a different second location on the inner edge of the sealing flap.

2. The facial sealing segment of claim 1, wherein the sealing flap comprises a first thickness and wherein the tear portion comprises a localized thickness less than the first thickness.

3. The facial sealing segment of claim 1, wherein the tear portion comprises a groove formed in the sealing flap.

4. The facial sealing segment of claim 3, wherein the groove is formed in a surface of the sealing flap opposite from a surface which sealingly engages the face of the user.

5. The facial sealing segment of claim 1, wherein the tear portion comprises a plurality of perforations formed in the sealing flap.

6. The facial sealing segment of claim 1, wherein the number of removable portions comprise a first portion adapted to be disposed adjacent a first side of the mouth of the user and a second portion adapted to be disposed adjacent a second side of the mouth of the user.

7. The facial sealing segment of claim 1, wherein at least one removable portion of the number of removable portions comprises a pull tab extending from a surface of the sealing flap opposite from a surface which sealingly engages the face of the user.

8. The facial sealing segment of claim 1, wherein at least one removable portion of the number of selectively removable portions comprises a sub-removable portion formed about the cutout, the sub-removable portion being defined in the at least one removable portion by a sub-tear portion.

9. The facial sealing segment of claim 1, wherein:
    the cutout comprises a first cutout adapted to receive the mouth of the user;
    the sealing flap is further disposed about, and defines, a second cutout adapted to receive the nares of the user; and
    the sealing segment further comprising a number of further removable portions formed in the sealing flap about the second cutout, each further removable portion being defined by a further tear portion.

10. A method of customizing a sealing segment of a respiratory device, the method comprising:
    providing a sealing segment comprising:
        a sealing flap adapted to engage the face of a user, the sealing flap having an inner edge that is disposed about, and defines a cutout adapted to receive one or both of the mouth or nares of the user, and
        a number of selectively removable portions formed in the sealing flap about the cutout, each removable portion being defined in the sealing flap by a tear portion that extends along a smooth curving line from a first location on the inner edge of the sealing flap to a different second location on the inner edge of the sealing flap; and removing at least one removable portion of the number of selectively removable portions by separating the at least one removable portion from the remainder of the sealing flap by severing along the tear portion.

11. The method of claim 10, wherein removing at least one removable portion of the number of selectively removable portions by separating the at least one removable portion from the remainder of the sealing flap by severing along the tear portion comprises removing a first removable portion from a first side of the cutout and removing a second removable portion from a second side of the cutout generally opposite the first side.

12. The method of claim 11, wherein removing at least one removable portion of the number of selectively removable portions by separating the at least one removable portion from the remainder of the sealing flap by severing along the tear portion comprises removing a portion of the sealing flap which is adapted to be disposed about the bridge of the nose of the user.

* * * * *